United States Patent [19]

Twardzik et al.

[11] Patent Number: 4,590,003

[45] Date of Patent: May 20, 1986

[54] PLATELET RELATED GROWTH REGULATOR

[75] Inventors: Daniel R. Twardzik, Bainbridge Island; George J. Todaro, Seattle, both of Wash.

[73] Assignee: Oncogen, Seattle, Wash.

[21] Appl. No.: 592,969

[22] Filed: Mar. 23, 1984

[51] Int. Cl.[4] .......................... C07K 7/06; C07K 7/08; C07K 7/10; C12N 5/00; C12N 5/02
[52] U.S. Cl. ..................... 530/330; 435/240; 435/241; 530/328; 530/326; 530/324; 530/351
[58] Field of Search ................... 260/112 R, 112.5 R; 435/240, 241

[56] References Cited

U.S. PATENT DOCUMENTS 4,479,896  10/1984  Antoniades ..................... 260/112 R

OTHER PUBLICATIONS

J. Physiol. (1979) 99 (3) pp. 395–406.
Proc. Nat'l. Acad. Sci., 76, (1979) 1809–1813.
Biochim et Biophysica Acta, 560 (1979) 217–241.
Proc. Nat'l. Acad. Sci., 76, 3722–3726 (1979).

*Primary Examiner*—Delbert R. Phillips
*Attorney, Agent, or Firm*—Bertram I. Rowland

[57] ABSTRACT

Polypeptide compositions are provided which inhibit human tumor cell growth. The compositions may be obtained from mammalian blood platelets by selective extraction and purification procedures and are shown to inhibit tumor growth in vitro.

5 Claims, No Drawings

PLATELET RELATED GROWTH REGULATOR

BACKGROUND OF THE INVENTION

1. Field of the Invention

The complexity of the regulation of differentiation and proliferation of and by hematopoietic cells is becoming increasingly apparent, as the list of factors controlling these events which are isolated continuously increases. For the most part, these factors are present in extraordinarily minute amounts in conjunction with numerous other proteins which serve a wide variety of functions. Factors which have been isolated and demonstrated to have activity include such polypeptides and proteins as γ-interferon, platelet-derived growth factor, colony stimulating factor, interleukin-2, erythropoietin, as well as numerous other lymphokines. There is substantial interest in the isolation, purification and characterization of these blood components because of their possible use in treatment, as well as their use in elucidating such diseases as cancer.

There are many pitfalls in isolating a naturally occurring factor. A system of separation must be developed which separates the desired factor from other factors which are present and may have similar characteristics. Secondly, some means for assaying the various fractions must be provided which specifically or substantially specifically characterizes the material of interest, in contrast to the other materials which are present. Where the polypeptide of interest has extraordinarily high activity, the difficulty of isolating the desired product is greatly enhanced. Thirdly, one must provide procedures which do not detrimentally affect the product of interest, particularly avoiding any denaturation. In addition, there are frequently other materials in the composition which may act upon the material of interest, changing it, so that the product which is ultimately obtained, which may have some of the desired activity, is not the naturally occurring material. Finally, after isolating the desired component in sufficiently pure form, one must then attempt to physically characterize the polypeptide, for example, by amino acid sequencing, glycosylation number, disulfide bridges, and the like. One must further characterize the material as to its physiological characteristics.

2. Description of the Prior Art

Holley, et al., Proc.Natl.Acad.Sci., U.S.A. (1980) 77:5989–5992, describe the purification of epithelial cell growth inhibitors. Nelsen-Hamilton and Holley, ibid. (1983) 80:5636–5640, describe the effect of a growth inhibitor and epidermal growth factor in the incorporation of radiotagged methionine into proteins secreted by African green monkey cells (BSC-1).

SUMMARY OF THE INVENTION

Novel compositions consisting primarily of a novel polypeptide, oncostatin-P, or degradation products or analogs thereof are provided. The oncostatin-P is isolated in at least substantially pure form and demonstrated to show physiological activity as a growth inhibitory factor. The oncostatin-P is derived from human platelets.

DESCRIPTION OF THE SPECIFIC EMBODIMENTS

Novel compositions of naturally occurring polypeptides or derivatives or analogs thereof are provided which provide for mammalian cell growth inhibition, e.g., tumor cell growth inhibition. The subject polypeptides are related to a naturally occurring polypeptide in the ethanolic HCl fraction obtained by extraction of platelets. The polypeptides are stable at moderate temperatures (0°–25° C.), at a low pH, generally below about pH 3, usually at pH 2. The polypeptides have a molecular weight in the range of about 5,000–8,000, more exactly in the range of about 6,000–7,500, more particularly about 7,000. The pure naturally occurring polypeptide is referred to as oncostatin-P. This polypeptide can be obtained from platelets of higher mammals, particularly primates, more particularly humans.

The polypeptide compositions of this invention can be obtained in high purity as established by sensitive bioassays. The polypeptide compositions can provide at 1 nanogram levels at least about 20% inhibition of tumor cell growth, particularly of carcinomas and sarcomas, e.g., of the lung, breast, skin, etc., preferably at least about 40%, and more preferably at least about 50%, inhibition of tumor cell growth in accordance with the colony inhibition test described in the Experimental. The polypeptide composition will have less than about 20%, more usually less than about 10%, and preferably less than about 5% by weight of polypeptides other than the major constituent present in the composition.

The polypeptides will for the most part have from about 60 to 80 amino acids, usually 60 to 75, more usually 65 to 72 and particularly 68 to 72, more particularly 69, 70 or 71 amino acids. The polypeptides will usually have a sequence, particularly a biologically active or epitopic sequence, more particularly at the N-terminus, which has the formula of the pentapeptide E-A-E-E-D, more usually the decapeptide E-A-E-E-D-G-D-L-Q-C, frequently the pentadecapeptide E-A-E-E-D-G-D-L-Q-C-L-C-V-K-T, and more frequently having the following formula:

E-A-E-E-D-C-D-L-Q-C-L-C-V-K-T-T-S-Q-V-R-P-R-H- where the letters have the following meaning in accordance with convention:

| | |
|---|---|
| A - alanine | L - leucine |
| C - cysteine | P - proline |
| D - aspartic acid | Q - glutamine |
| E - glutamic acid | R - arginine |
| G - glycine | S - serine |
| H - histidine | T - threonine |
| | V - valine |

The compositions can find use both in vitro and in vivo. The compositions can be used to inhibit cell growth in an in vitro system. Thus, the subject compositions can be used an an agonist or antagonist in evaluating other growth factors, both mitogens and growth inhibitors. The subject compositions can also be used for slowing mammalian growth in culture, so as to reduce the energy expenditure for multiplication of the cells, as contrasted to producing a desired product.

Oncostatin-P can be formulated in physiologically acceptable carriers, such as phosphate buffered saline, distilled water, excipients, or the like, or may be employed neat.

The subject composition can be obtained by extraction of platelets with approximately 0.3M ethanolic hydrochloric acid. As inhibitors against degradation, phenylmethylsulfonyl fluoride and aprotinin may also be included, the former at levels of about 1–10% by weight of the extracting composition and the latter at levels of about 0.1–1 TIU/mg (TIU—trypsin inhibition units) of the extracting composition and the latter at levels of about 0.1–1 TIU/mg of the extracting composition. After raising the pH to about 5, using aqueous ammonium hydroxide, a small amount of ammonium acetate is added and the solution clarified by centrifugation or other convenient means.

The protein is then precipitated by successively employing cold ethanol (95%) and ether, the precipitate collected and dialyzed against 0.1–0.5M acetic acid employing a dialysis membrane having a cutoff below about 5,000M weight. The residue is lyophilized, resuspended in 1M acetic acid, clarified and is then ready for further purification by gel permeation chromatography employing Biogel P-10. The product is eluted with about 1M acetic acid and the various fractions monitored employing an appropriate assay technique, e.g., tumor growth inhibition.

The fractions having the growth inhibiting activity are lyophilized, resuspended in dilute aqueous trifluoroacetic acid, pH 2–3, clarified and then chromatographed on a high pressure, liquid chromatograph, where the silica packing has a coating of a long aliphatic chain of from about 16 to 20 carbon atoms, e.g., 18 carbon atoms. The column is equilibrated with dilute trifluoroacetic acid (0.02–0.1%) and the product eluted with an acetonitrile gradient of up to 60% acetonitrile in dilute (0.01–0.1, usually about 0.04–0.05%) trifluoroacetic acid. A relatively slow flow rate is employed, generally about 0.5 to 1 m/min. at ambient temperatures. The fractions may be assayed by the bioassay indicated previously or other bioassays. For further purification, the product obtained from the column may be purified utilizing high pressure gel exclusion chromatography.

The major peak of oncostatin-P activity resolved by Novapak $C_{18}$ reverse phase liquid chromatography was lyophilized and resuspended in 100 μl of 40% acetonitrile containing 0.1% trifluoroacetic acid. The sample was injected into a hydroxylated polyether gel column (Bio Rad TSK-250) and eluted with a mobile phase consisting of 40% acetonitrile in 0.1% trifluoroacetic acid. Aliquots of each fraction were lyophilized and tested for oncostatin-P activity; tumor cell inhibition activity coeluted with the major peptide peak (Rf - 0.9), which also corresponds in molecular weight to that of the 6,000Mr insulin marker used to calibrate this chromatographic system.

The product obtained from the column may be electrophoresed employing SDS-PAGE. The band at about 6,000–8,000 molecular weight is isolated. The band is shown to have strong growth inhibitory activity against mammalian cells, e.g., tumor cells.

The following examples are offered by way of illustration and not by way of limitation.

EXPERIMENTAL

Abbreviations: DMEM—Dulbecco's modified Eagle's medium, PBS phosphate buffered saline; P/S—penicillin/streptomycin (0.57 mg/ml each); FCS—fetal calf serum; SDS-PAGE—sodium dodecylsulfate polyacrylamide gel electrophoresis.

A. Purification of Oncostatin-P

Acid-ethanol Extraction from Human Platelets

Fresh or frozen platelets (50 g-wet weight) thawed at room temperature were resuspended in two volumes of: 375 ml ethanol (95%), 7.5 ml conc. HCl, 33 mg phenylmethylsulfonyl fluoride and 1 ml of aprotinin (23 TIU/ml; from bovine lung—Sigma Chemical Co. A6012). The mixture was stirred at 4° C. overnight, centrifuged 8K rpm in Beckman-type 19 rotor for 30 min. and the supernatant removed. The pH of the supernatant was adjusted with conc. ammonium hydroxide to 4.0 and the pH raised to 5.2 using a 1:10 dilution of conc. ammonium hydroxide. After adding 1 ml of 2M ammonium acetate (pH 5.2) per 0.1 L of supernatant, the solution was centrifuged 8K rpm in type 19 rotor for 30 min. The supernatant was removed, a 2×volume cold 95% ethanol added, followed by a 4×volume cold diethyl ether and the mixture allowed to stand overnight at 0° C. The precipitate was collected by centrifuging at 8K rpm type 19 rotor for 30 min. and the pellet was suspended in about 10–20 ml of 1M acetic acid. The acetic acid dispersion was dialyzed extensively against 5 L×2 changes of 0.2M acetic acid in a Spectrapor dialysis membrane (#3) tubing (cutoff 3,500MW) (American Scientific Products). The extract was lyophilized, resuspended in 7.5 ml of 1M acetic acid, followed by centrifuging at 30K rpm.

Gel Permeation Chromatography

Biogel P-10 (200–400 mesh; Bio Rad Labs) was swelled overnight in 1M acetic acid, degassed thoroughly and then poured into a 100×2.5 cm siliconized glass column and allowed to equilibrate overnight with 1M acetic acid. All solutions were degassed before using.

The acid-ethanol solubilized peptides (50–70 mg of protein) from 25 g of human platelets were dissolved in 7.5 ml of 1M acetic acid and applied to the above column. Fractions (3.5 ml) were collected and aliquots were lyophilized and tested for inhibition of 5-$^{125}$I-iodo-2'-deoxyuridine incorporation into A549 human lung carcinoma cells.

Reverse-phase High-pressure Liquid Chromatography

The fraction containing the peak of tumor growth inhibitory activity (about 200 μg of protein) from the above column was lyophilized and resuspended in 0.05% (v/v) of trifluoroacetic acid. The column was then eluted with a linear 0–60% gradient of acetonitrile in 0.045% trifluoroacetic acid at a flow rate of 0.8 m/min at 23° C. Aliquots of each fraction were lyophilized and assayed in triplicate, as described above.

The fraction(s) containing the inhibitory activity were then dissolved in 40% acetonitrile containing 0.1% trifluoroacetic acid and applied to a hydroxylated polyether gel column (Bio Rad TSK-250) and eluted with a mobile phase of 40% acetonitrile in 0.1% trifluoroacetic acid. Fractions were collected, lyophilized abd assayed in triplicate for growth inhibitory activity. The activity elutes in the fraction where the insulin marker elutes and corresponds to a molecular weight of 6–8 kilo-daltons.

Those fractions having the highest activity were then electrophoresed employing SDS-PAGE as follows.

The peptide corresponding to the major oncostatin-P activity from the reverse phase high performance liquid chromatography purification step was lyophilized, resuspended and boiled (2 min.) in 0.03 ml of a sample preparation buffer containing 12.5 mM Tris-Cl pH 6.7, 4% SDS, 10% β-mercaptoethanol, 20% glycerol and 0.01% Bromphenol Blue. The sample was loaded onto a 5% polyacrylamide stacking gel poured over a 17 to 27% polyacrylamide gradient slab gel containing 0.1% SDS and pH 8.8. The gel was run at 10 milliamps until samples migrated through the stacking gel and at 20 milliamps until the dye front migrated to the bottom of the gel. Gels were fixed and stained overnight in a solution of 0.2% Coomassie blue, 50% methanol and 9% acetic acid. Following destaining, Coomassie positive bands were localized utilizing a Hoffer densitometer. Markers included insulin (6,000$M_r$), trypsinogen, (24,500 $M_r$), RN'ase (13,700$M_r$), and aprotinin (6,500$M_r$). The major peptide comigrated with the 6,500$M_r$ aprotinin standard under these conditions of electrophoresis.

The assay employed was on day 2 in the morning to set up A549 (human lung carcinoma) cells in Nunc 96 well plates (Kamstrupvej 90. DK-4,000, Roskilde, Denmark). These cells were passaged when there were fewer than 30. Into all but the peripheral wells was introduced 45,000 cell/50 μl well ($9 \times 10^4$ cells per ml DMEM with 10% FCS, P/S. glutamine). The peripheral wells received 50 μl PBS and the entire plate was incubated at 37° C. In the afternoon, the test samples were resuspended in DMEM with 10% FCS, P/S, glutamine for triplicate testing. Into each test well was delivered 50 μl while control wells received 50 μl DMEM and the plate incubated at 37° C. for 3 days. On day 4, into each well 50 ml of a solution of $^{125}$I-iodo-2'-deoxyuridine (4 Ci/mg-0.5 mCi/ml) (1 μl isotope/ml DMEM containing 10% FCS, P/S, glutamine) and the plate incubated at 37° C. overnight. On day 5, the medium was aspirated from the wells, washed 1× with PBS, 100 μl methanol added, the methanol allowed to stand for 10 min. followed by aspiration of the methanol. To the wells was then added 200 μl, 1M sodium hydroxide, the plate incubated for 30 min. at 37° C. and then 1M sodium hydroxide removed with Titertek plugs (Flow Labs). The plugs were then counted in a gamma counter for radioactivity.

To demonstrate the effectiveness of the oncostatin-P prepared above, the following test was carried out. The test is referred to as soft agar colony inhibition. The materials employed are 5% agar (3.75 g Nobel agar (Difco)). 75 ml of distilled water, autoclaved in a 125 ml Wheaton bottle. DMEM with 10% FCS, 100 U penicillin, 100 U streptomycin, 200 mM glutamine, and human melanoma cells (A375).

Materials to be tested are lyophilized in a sterile 12×75 mm test tube. A 1:10 dilution of the 5% agar is made with DMEM and heated to 46° C. in a water bath. A base layer is prepared by pipetting 1 ml of 0.5% agar solution into each well of a 6 well culture plate (35×14 mm). The layer is allowed to stand at room temperature until it hardens. SA$_6$ cells are prepared by trypsinizing and the number of cells counted. The cells are diluted to a final concentration of $1 \times 10^4$ cells per ml and 0.35 ml. of cells is added to each test sample tube.

Into each of ten test sample tubes is pipetted 0.750 ml of a 0.5% agar solution, the mixture vortexed gently and the contents of the test tube (test sample, cells, agar) is poured onto the base layer and allowed to stand for about 20 min. at room temperature until the agar hardens. The plates may then be stored in a 37° C. humidified incubator with 5% carbon dioxide.

The plates are checked for inhibition of colony growth after 3 days and up to 10 days depending on the potency of the test material. The number of colonies is counted in 8 random low power microscope fields. When plates are to be maintained longer than 5 days, another 1 ml layer of 0.3% agar solution should be overlayed on the test sample layer to prevent drying of the test sample layer.

The above procedure was employed using varying concentrations of the purified oncostatin-P. The following table indicates the results, the amount of oncostatin-P indicated being the lyophilized amount introduced into the test tube. The results are reported as percent maximal inhibition.

TABLE I

| Oncostatin-P $\log_{10}$ng | Maximal inhibition % |
|---|---|
| 0.8 | 45 |
| 0.26 | 73 |
| 20 | 81 |
| 60 | 100 |

It is evident from the above results, that the subject polypeptide is a potent inhibitor of cell growth. Based on the results observed with the melanoma cells, about 1 nanogram is sufficient to provide about 50% inhibition. The subject compound can, therefore, find a wide variety of uses in inhibiting cellular growth, including neoplastic cellular growth. For example, the subject compound also inhibits a variety of cultured human tumor cells, but not normal non-neoplastic human foreskin fibroblasts, as evidenced in the following table.

TABLE II

| Effect of Oncostatin-P on in vitro DNA synthesis in cultured human cells | |
|---|---|
| Cell Line | % Maximal[a] inhibition of $^{125}$I-deoxyuridine incorporation |
| Transformed | |
| Human carcinoma of lung (A549) | 100 |
| Human adenocarcinoma of lung (H125) | 41 |
| Human melanoma (A375) | 67 |
| Human Carcinoma of breast (MCF-7) | 37 |
| Non Transformed | |
| Human foreskin fibroblast (HuF$_{p6}$) | 0 |

[a]Utilizing the assay conditions described, the maximum inhibition of $^{125}$I-deoxyuridine incorporation into A549 cells observed at saturating concentrations of hTGIFp (≃ ng/well) does not exceed 50 percent relative to untreated control cultures.

Although the foregoing invention has been described in some detail by way of illustration and example for purposes of clarity of understanding, it will be obvious that certain changes and modifications may be practiced within the scope of the appended claims.

What is claimed is:

1. A composition being at least about 90% by weight of oncostatin-P, wherein said oncostatin-P is characterized by having a molecular weight of about 7000, being isolatable by extraction of platelets with approximately 0.3M ethanolic hydrochloric acid, precipitation with cold ethanol and ether and dialysis against 0.1–0.5M acetic acid and gel permeation chromatography employing Biogel P-10 and 1M acetic acid eluent, and having substantially the following sequence at its N-terminus: glu-ala-glu-glu-asp and capable of inhibiting tumor cell growth in the colony inhibition test.

2. Oncostatin-P substantially free of other cellular components.

3. A method of inhibiting cellular growth, which comprises applying an effective amount for inhibition of a polypeptide composition according to claim 1 to proliferating cells.

4. A method according to claim 3, wherein said cells are carcinoma cells.

5. A method according to claim 3, wherein said proliferating cells are in culture.

* * * * *